United States Patent
Braverman et al.

(10) Patent No.: US 6,416,487 B1
(45) Date of Patent: *Jul. 9, 2002

(54) METHOD OF REMOVING BETA-2 MICROGLOBULIN FROM BLOOD

(75) Inventors: Andrew Braverman, New York, NY (US); Vadim Davankov, Moscow (RU)

(73) Assignee: Renal Tech International LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/294,224

(22) Filed: Apr. 19, 1999

Related U.S. Application Data

(63) Continuation-in-part of application No. 08/902,727, filed on Jul. 30, 1997, now Pat. No. 5,904,663.

(51) Int. Cl.[7] .......................... A61M 5/00; A61M 1/14; B01D 15/00; B01J 20/26
(52) U.S. Cl. ................. 604/5.01; 422/44; 210/679; 210/905; 502/402
(58) Field of Search ................ 604/4–6, 4.01, 604/5.01–5.04, 6.09, 6.11; 210/645–646, 767, 679, 635, 660, 691, 502.1, 905; 422/44; 128/898; 502/400–402; 521/30, 31, 25, 73, 75

(56) References Cited

U.S. PATENT DOCUMENTS

| | | | | |
|---|---|---|---|---|
| 5,051,185 A | * | 9/1991 | Watanabe et al. | 210/635 |
| 5,073,265 A | * | 12/1991 | Johnson et al. | 210/500.23 |
| 5,403,750 A | * | 4/1995 | Braatz et al. | 436/531 |
| 5,773,384 A | * | 6/1998 | Davankov et al. | 502/402 |
| 5,904,663 A | * | 5/1999 | Braverman et al. | 604/5.01 |

* cited by examiner

Primary Examiner—Angela D. Sykes
Assistant Examiner—Patricia Bianco
(74) Attorney, Agent, or Firm—I. Zborovsky

(57) ABSTRACT

A method of removing beta-2 microglobulin from blood, plasma and the like, has the steps of removing blood from a patient, passing the blood through an ADSORBENT material with a size and a structure selected so as to remove beta-2 microglobulin from the blood, and re-entering the blood from which the beta-2 microglobulin is removed into the patient.

5 Claims, No Drawings

METHOD OF REMOVING BETA-2 MICROGLOBULIN FROM BLOOD

CROSS-REFERENCE TO A RELATED APPLICATION

This application is a continuation-in-part of patent application Ser. No. 08/902,727 filed on Jul. 30, 1997, now U.S. Pat. No. 5,904,663.

BACKGROUND OF THE INVENTION

The present invention relates to a method of removing beta-2 microglobulin from blood, plasma and other physiological liquids of organism.

Beta-2 microglobulin, a protein, is found in abnormally high concentrations in physiological fluids of patients with chronic renal failure and on chronic dialysis. Beta-2 microglobulin is removed by the kidneys in the proximal tubes by endocytosis in a healthy individual. The molecule is the co-dimer in the dimeric structure of Class-1 HLA antigens. These antigens are found in high concentration on lymphocytes and are found on all nucleated mammalian cells. In patients with malfunctioning kidney, beta-2 microglobulin accumulates to 40 to 60 multiples of normal. The accumulation of beta-2 microglobulin is basis of the initiation of Dialysis-Associated Amyloidosis. This is a clinical entity that causes arthropathy and neuropathy. The primary effect is severe joint destruction and pain. Many patients require corrective surgery such as Carpal-Tunnel Laminectomies and Cervical Spine Laminectomy. In addition, they require use of analgesics and anti-inflammatory medications to treat the symptoms of DRA.

Attempts to remove beta-2 microglobulin have been made, as disclosed for example in A New Therapeutic Approach to Dialysis Amyloidosis: Intensive Removal of $\beta_2$-Microglobulin with Adsorbent Column by Fumitake Geijyo, Noriyuki Homma, Shin Hasegawa, and Massaaki Arakawa published in Department of Internal Medicine (II), Niigata University School of Medicine, Niigata, Japan. A method of removing beta-2 microglobulin from blood is also disclosed in our U.S. patent application Ser. No. 08/902,727 filed on Jul. 30, 1997, now U.S. Pat. No. 5,909,663. This method can be further amplified and improved.

SUMMARY OF THE INVENTION

Accordingly, it is an object of present invention to provide a method of removal of beta-2 microglobulin, which is a further improvement of existing methods.

In keeping with these objects and with others which will become apparent hereinafter, one feature of present invention resides, briefly stated, in a method of removal of beta-2 microglobulin in accordance with which a blood is passed through an adsorbent material which has a pore size and a structure selected so as to remove beta-2 microglobulin from blood, and the blood from which the beta-2 microglobulin is removed is reentered into the patient.

In accordance with a preferable embodiment of the present invention, the passing of the blood through the adsorbent material can take place simultaneously with the conventional hemodialysis procedure, where the blood is forced to pass in sequence through the adsorbent material and through the hemodialysis membrane cartridge.

In accordance with still a further feature of the present invention, the adsorbent material is a porous polydivinylbenzene or polystyrene-co-polydivinylbenzene polymer with an enhanced proportion of mesopores.

In accordance with still a further feature of the present invention, the passing includes passing through the adsorbent material which is a porous polydivinylbenzene or polystyrene-co-polydivinylbenzene polymer with an enhanced proportion of mesopores and with a surface of the beads and of macropores modified so as to prevent absorption of large proteins and platelets and to minimize activation of blood complement system without affecting noticeably accessibility of an inner absorption space of the beads for beta-2 microglobulin and middle-sized toxicant molecules.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF PREFERRED EMBODIMENTS

In accordance with present invention, a method of removing beta-2 microglobulin from blood, plasma and other physiological liquid of organism is proposed. A patient's blood is withdrawn from an arterial blood circulatory access point, and passed through an adsorbent material—polymer.

In accordance with the present invention, the passing of the blood through the adsorbent material can take place simultaneously with the conventional hemodialysis procedure, where blood is forced to pass through the adsorbent material and then through a hemodialysis membrane cartridge, or vice versa.

The adsorbent material through which the blood passes can be a porous polydivinylbenzene or polystyrene-co-polydivinylbenzene polymer with an enhanced proportion of mesopores.

Also, the adsorbent material can be a porous polydivinylbenzene or polystyrene-co-polydivinylbenzene polymer with an enhanced proportion of mesopores and with a surface of the beads and of macropores modified so as to prevent adsorption of large proteins and platelets and to minimize activation of blood complement system without affecting noticeably accessibility of an inner adsorption space of the beads for beta-2 microglobulin and middle-sized toxicant molecules.

In accordance with this invention sorbents prepared in accordance with the invention are charged to a column or cartridge for service. The column should preferably be provided with an inlet and an outlet designed to allow easy connection with the blood circuit, and with two porous filters set between the inlet and the sorbent layer, and between the sorbent layer and the outlet. The column may be made of a biocompatible material, glass, polyethylene, polypropylene, polycarbonate, polystyrene. Of these, polypropylene and polycarbonate are preferred materials, because the column packed with the sorbent can be sterilized (e.g., autoclave and gamma-ray sterilization) before use.

The column or cartridge is then filled with a 1% solution of human serum albumin in normal saline and stored at 4° C. When ready for use, the column is washed with 0.9% NaCl solution to which has been added a suitable anticoagulant, such as ACD-A containing heparin in an effective amount. For a 250 ml cartridge, this is approximately 1 l of the sodium chloride solution to which 150 ml of ACD-A containing 6,000 units of heparin has been added.

As usual the following two typical extracorporeal blood circulation systems can be employed:

(I) Blood taken from a blood vessel of a patient is forced to pass through a column packed with the sorbent of this invention, and the clarified blood is returned to the blood vessel of the patient.

(ii) Blood taken from a patient is first separated through a separation membrane, by centrifugation or the like into hemocytes and plasma, the plasma thus separated is then forced to pass through the column packed with the sorbent of this invention to remove toxicants from the plasma; then, the clarified plasma from the column is mixed with the hemocytes separated above, and the mixture is returned to the blood vessels of the patient.

The preparation of the adsorbent material can be performed as follows:

EXAMPLE 1

A solution of 130 g p-ethylstyrene, 132 g divinylbenzene (a mixture of para and metha-isomers of about 1:1) and 2.62 g benzoyl peroxide in a mixture of 600 ml toluene and 100 ml iso-amyl alcohol was suspended in 4 liters of pure water containing 1% cellulose stabilizer. After 39 min stirring at room temperature, the mixture was heated at 40° C. for 1 hours, 60° C. for 2 hours, 80° C. for 5 hours and 96° C. for 2 hours. After cooling the mixture to room temperature, the beads obtained were filtered and washed with hot water, methanol and water. The polymer was dried in oven for 7 hours at 80° C.

The polymer obtained in Example 1 displayed apparent inner surface area of 1200 sq.m/g and total pore volume of 0.8 ml/g, increased its volume in ethanol by a factor of 1.3, adsorbed Cytochrome C from a phosphate buffer solution in an amount of 32–34 mg per 1 g of the polymer, efficiently removed beta2-microglobuline from blood of patients on permanent dialysis treatment, did pass successfully the hemocompatibility test (recalcification of plasma within the allowed 126–144 sec time limits) without any chemical modification or additional treatment of the surface of polymeric beads. Individual spherical beads of the polymer of 0.4–0.63 mm in diameter were mechanically destroyed at a loading of 450 m 50 g, which is much better as compared to typical macroporous beads (about 120–150 g), but not as good as typical hypercrosslinked beads (up to 600 g) of a comparable diameter and total porous volume.

EXAMPLE 2

Into a seven-liter four-necked round-bottom flask equipped with a stirrer, a thermometer and a reflux condenser, is placed the solution of 8.4 g polyvinyl alcohol-type technical grade emulsion stabilizer GM-14 in four liters of deionized water (aqueous phase). The solution of 260 ml divinylbenzene, 140 ml ethylvinylbenzene, 250 ml toluene, 250 ml n-octane and 2.94 g benzene peroxide (organic phase) is then added to the aqueous phase on stirring at room temperature. In 20 min, the temperature is raised to 80° C. The reaction is carried out at 80° C. for 8 hours and 90–92° C. for additional 2 hours. After accomplishing the copolymerization, the stabilizer is rigorously washed out with hot water (60 to 80° C.) and the above organic solvents are removed by steam distillation. The beads obtained are filtered, washed with 1 l dioxane and with deionized water. Finally, the beads are dried in oven at 60° C. overnight.

EXAMPLE 3

As in Example 1, taking 220 ml divinylbenzene, 180 ml ethylvinylbenzene, 150 ml toluene, 150 ml n-octane and 3.0 g benzene peroxide as the organic phase. Inner surface area of the product obtained amounts to 1000 sq.m/g, Volume swelling with ethanol amounts to 1.25.

EXAMPLE 4

As in Example 1, taking organic phase consisting of 320 ml divinylbenzene, 80 ml ethylvynylbenzene, 600 ml toluene, 600 ml n-octane and 2.94 g bis-azoisobuthyric nitrile. Inner surface area of the product obtained amounts to 1150 sq.m/g. Volume swelling with ethanol amounts to 1.5.

EXAMPLE 5

As in Example 1, taking 250 ml benzene and 250 ml methanol, instead of toluene and n-octane, as the porogen for the preparation of organic phase. Inner surface area of the product obtained amounts to 800 sq.m/g. Volume swelling with ethanol amounts to 1.3.

EXAMPLE 6

As in Example 1, taking 200 ml ethylene dichloride and 120 ml n-hexane as the porogen. Inner surface area of the product obtained amounts to 1000 sq.m/g. Volume swelling with ethanol amounts to 1.3.

EXAMPLE 7

As in Example 1, taking the mixture of 400 ml cyclohexane and 100 ml methanol as the porogen. Inner surface area of the product obtained amounts to 800 sq.m/g. Volume swelling with ethanol amounts to 1.2.

In accordance with the present invention, as explained herein above, the surface of the beads of the polymer can be modified. In particular, surface exposed vinyl groups are chemically modified so as to form different surface exposed functional groups with a greater hydrophilicity and greater biocompatibility than those of vinyl groups.

The modification of the copolymers can be performed in accordance with the following three principal directions: grafting hydrophilic polymer chains by a radial polymerization of 2-hydroxyethyl methacrylate, N-vinylpyrrolidone, N-vinylcaprolactame, or other water soluble monomers, oxidation of the vinyl groups to epoxy groups with the subsequent reaction of the epoxy groups with water, ethylene glycol, amines, 2amonoethanol or amino acid molecules, and depositing high-molecular-weight hemocompatible polymer, in particular poly(trifluorethyoxy) phosphazene onto the surface of the polymeric beads.

This was disclosed in detail in our patent application Ser. No. 09/019,583 which is incorporated here by reference.

Several examples of the modification procedure are presented herein below.

EXAMPLE 1

(Aqueous-organic Medium)

5.4 g of the water-washed polymer (dry weight 2.1 g), prepared by polymerization of technical grade 50%-divinylbenzene described in Example 1, were suspended in a mixture of 3 ml ethanol and 2 ml water and supplied with a solution of 0.05 g of ammonium persulfate in 2 ml water, a solution of 0.035 ml tetramethyl ethylenedlamine in 1 ml ethanol and finally with a solution of 0.03 ml N-vinylpyrrolidone in 1 ml ethanol. The mixture was stirred at 37° C. for 4 hours. Using spectrophotometry at 234 nm, 99% of the initial amount of vinylpyrrolidone were found to graft to the polymer in the above aqueous/ethanolic mixture of the appropriate composition of 7:5 (vol/vol). The final polymer was washed with ethanol and dried to constant weight. The dry polymer can be easily wetted with water, what indicates the presence of hydrophilic'grafted polymer layer on the surface of the basically hydrophobic material.

EXAMPLE 2
(Organic Medium)

68 g of dry polymer obtained by polymerization of technical-grade 50%-divinylbenzene according to the protocol described in the above Example 1, were suspended in 350 ml ethanol, supplied with a solution of 1.4 g azo-bis-isobutyro nitrile in 60 ml ethanol, and heated to 60° C. At that temperature the mixture was provided with a solution of 1.0 ml N-vinylpyrrolidone in 10 ml ethanol. After shaking the mixture at 60° C. for 3.5 hours, conversion of vinylpyrrolidone was found to reach 99%. The final polymer thus contained 1.5% polyvinylpyrrolidone.

EXAMPLE 3
(Organic Medium)

To 1.5 g dry polymer of Example 1 suspended in 5 ml methanol at 40° C. were added 0.04 g layroyl peroxide in 2 ml methanol and 0.01 ml tetramethyl ethylenediamine in 1 ml methanol. The mixture was heated to 50° C. for 1 hr, supplied with 0.01 ml N-vinylpyrrolidone in 1 ml methanol and heated further to 60° C. for 3 hours. The polymer was washed with methanol and dried.

EXAMPLE 4
(Organic Medium)

To 2 g dry polymer of Example 1 suspended in 10 ml dioxane a solution of 0.08 g lauroyl peroxide in 4 ml ethanol was added. The temperature of the mixture was increased to 60° C. within 10 min, before additional 2 ml dioxane which contained 0.02 ml N-vinylpyrrolidone were added. The reaction mixture was stirred for 3 hr at 60° C. and the polymer was filtered and washed with ethanol.

EXAMPLE 5
(Organic Medium)

2 g of dry polymer described in Example 1 and suspended in 10 ml ethanol were added at 40° C. with 0.08 g lauroyl peroxide in 4 ml ethanol. In 5 minutes 0.02 ml of tetramethyl ethylenediamine in 2 ml ethanol, and, after another 5 minutes, 0.02 ml N-vinylpyrrolidone in 2 ml ethanol were added. After shaking the mixture for 2.5 hours at 40° C., 80% of the initial vinylpyrrodone were found to be grafted to the polymer surface.

The medium which is used for modification of the polymers can be purely organic; however, it can be for example aqueous-organic and contain at least 20 vol. % of the organic substance.

It has been found that when modification procedure is performed in non-organic, purely aqueous medium, the polymer can be contaminated with endotoxins, and animals whose blood was purified through the thusly produced material developed fever, which can be considered as indirect indication of the presence of endotoxins in the polymer.

In contrast, numerous experiments conducted for purification of physiological liquids of organism with the use of materials modified with the utilization of the medium in accordance with the present invention showed that the polymers were not contaminated with endotoxins.

Depositing Polyphosphazene

EXAMPLE 6

A solution of 0.0009 g poly(trifluoroethoxy) phosphazene (molecular weight $10^7$) in 8 ml ethyl acetate were added quickly to 3 g of dry porous polymer and agitated until the whole of the solvent was totally absorbed by the polymer beads. The material was then dried under reduced pressure and washed with ethanol.

What is claimed is:

1. A method of removing beta-2 microglobulin from blood, comprising the steps of removing blood from a patient, passing the blood through an adsorbent material with a size and a structure selected so as to remove beta-2 microglobulin from the blood, and re-entering the blood from which the beta-2 microglobulin is removed into the patient, wherein said material is a porous beaded polydivinylbenzene or polystyrene-co-polydivinylbenzene polymer with a surface of beads and of pores modified so as to prevent adsorption of large proteins and platelets and to minimize activation of blood complement system without affecting noticeably accessibility of an inner absorption space of the beads for beta-2 microglobulin and middle-sized toxicant molecules, in which polymer surface exposed vinyl groups are chemically modified so as to form different surface exposed functional groups with a greater hydrophilicity and greater biocompatibility than those of the vinyl groups, so that during contact of blood with the material the beaded polymer provides adsorption of beta-2 microglobulin while the different surface exposed functional groups provide the biocompatibility of the material.

2. A method of removing beta-2 microglobulin from blood as defined in claim 1, wherein said passing the blood through said adsorbing material takes place simultaneously with a conventional hemodialysis procedure where the blood is forced to pass also through a hemodialysis membrane cartridge.

3. A method of removing beta-2 microglobulin from blood as defined in claim 1, wherein said passing the blood through said adsorbing material takes place in sequence with a conventional hemodialysis procedure where the blood is forced to pass also through the hemodialysis membrane cartridge.

4. A method as defined in claim 1, wherein said passing includes passing through the adsorbent material which is porous polydivinylbenzene or polystyrene-co-polydivinylbenzene polymer.

5. A method as defined in claim 4, wherein said polymer has an enhanced portion of mesopores.

* * * * *